United States Patent [19]

Komine et al.

[11] 4,456,902
[45] Jun. 26, 1984

[54] GAS AND HUMIDITY SENSING ELEMENT

[75] Inventors: Yoshiharu Komine; Takao Sawada, both of Amagasaki, Japan

[73] Assignee: Mitsubishi Denki Kabushiki Kaisha, Tokyo, Japan

[21] Appl. No.: 475,949

[22] Filed: Mar. 16, 1983

[30] Foreign Application Priority Data

Mar. 30, 1982 [JP] Japan .................................. 57-51826
Mar. 30, 1982 [JP] Japan .................................. 57-51827
Mar. 30, 1982 [JP] Japan .................................. 57-51828
Mar. 30, 1982 [JP] Japan .................................. 57-51854

[51] Int. Cl.$^3$ .......................... H01L 7/00; G01N 27/46
[52] U.S. Cl. ........................................ 338/34; 338/35; 204/412; 204/426
[58] Field of Search ............... 204/412, 421, 425, 426, 204/430, 431; 338/34, 35

[56] References Cited

U.S. PATENT DOCUMENTS

| 3,705,375 | 12/1972 | Hershler | 338/35 |
| 4,015,230 | 3/1977 | Nitta et al. | 338/35 |
| 4,052,691 | 10/1977 | Nagano et al. | 338/35 |
| 4,328,478 | 5/1982 | Murata et al. | 338/35 |
| 4,359,709 | 11/1982 | Nakatani et al. | 338/34 |

FOREIGN PATENT DOCUMENTS

| 9825 | 4/1980 | European Pat. Off. | 338/35 |
| 56199 | 5/1979 | Japan | 338/35 |
| 165508 | 12/1980 | Japan | 338/35 |

OTHER PUBLICATIONS

Journal of Electronic Materials, vol. 10, No. 3, 1981, R. B. Cooper et al., "Gas Sensing Mechanisms in SnO$_2$ Thin Films".

Primary Examiner—G. L. Kaplan
Assistant Examiner—Nam X. Nguyen
Attorney, Agent, or Firm—Oblon, Fisher, Spivak, McClelland & Maier

[57] ABSTRACT

A gas and humidity sensing element in a single integral structure made of a base plate of apatite ceramics, on which a particular metal oxide such as tin oxide, zinc oxide, or composite oxide of titanium and niobium is provided. The sensing element has a function of sensing gas and humidity with outstanding sensitivity to bad smell gas and alcoholic gas, in which the humidity is sensed and measured by variations in electrical resistance of the apatite ceramic base plate and the bad smell gas such as hydrogen sulfide, methyl mercaptan, etc. is sensed and measured by variations in electrical resistance of the metal oxide.

5 Claims, 13 Drawing Figures

GAS AND HUMIDITY SENSING ELEMENT

BACKGROUND OF THE INVENTION

1. Field of the Invention

This invention relates to an element for detecting bad smell gas, alcoholic gas, and humidity in the surrounding atmosphere.

2. Description of Prior Arts

There have so far been used various materials for the humidity detecting element, such as metal oxides, inorganic and organic electrolytes, and those substances utilizing the relative humidity dependent property of the electric conductivity of an organic substance dispersed in an electrically conductive material. Use of such materials has been considered from the standpoint of readiness in handling the element and its connectivity with a micro-processor. Of these various materials, the metal oxides are particularly preferred on account of their stability in operation and heat-resistance.

Measurement of concentration of methyl mercaptan ($CH_3SH$), hydrogen sulfide ($H_2S$) and others which are principal constituents of offensive odor to occur at the sewage disposing sites, refuse disposing sites, and so forth has so far been done in part by electro-chemical expedients. However, such electro-chemical processings require sampling of the gas and make the measuring operations complicated. On the other hand, conventional semiconductor gas sensors are not sufficient in their sensitivity and so have not yet found their way to the practical utilization.

For the element to detect alcoholic gas, there have also been used various kinds of material such as those utilizing variations in electrical conductivity of a metal oxide semiconductor due to their chemical adsorption of the gas. Such use is also from the standpoint of readiness in handling the element and its compatibility with a micro-processor. The material for constituting the element is selected from $SnO_2$, $ZnO$, and others. However, since these materials have almost same degree of sensitivity to various inflammable gases, the selective detection of alcoholic gas has been difficult.

Further, there has heretofore been no element in a single integral construction which is capable of detecting both humidity and gas, and yet has a stable humidity sensing characteristic and a gas sensing characteristic having a quick response speed with high sensitivity and high selectivity to those bad smell gases and alcoholic gas.

SUMMARY OF THE INVENTION

It is therefore an object of the present invention to provide a gas and humidity sensing element which is made of a single integral material and is capable of detecting a relative humidity in a range of from 0 to 100%, alcoholic gas, and bad smell gas such as methyl mercaptan ($CH_3SH$), hydrogen sulfide ($H_2S$), and others with high sensitivity and selectivity.

It is another object of the present invention to provide a gas and humidity sensing element which utilizes a metal oxide doped with ruthenium oxide, or which utilizes a base plate for the element, on which electrodes made of ruthenium oxide are printed and baked, thereby promoting increase in sensitivity of the element to those bad smell gas and alcoholic gas.

It is still another object of the present invention to provide a gas and humidity sensing element, in which humidity is detected by an apatite ceramics material, and the bad smell gas and alcoholic gas are detected by the metal oxide interposed between the separate electrodes provided on the element base plate constituted with the abovementioned apatite ceramics material.

It is an other object of the present invention to provide a gas and humidity sensing element which is capable of readily detecting relative humidity and/or bad smell gases or alcoholic gas by measuring electric resistance of the element, in view of the fact that its electrical resistance remarkably changes at a relative humidity in a range of from 0 to 100%, a bad smell gas concentration in a range of from 0 to 1,000 ppm or an alcoholic gas concentration in a range of from 0 to 3,000 ppm.

According to the present invention, in one aspect of it, there is provided a gas and humidity sensing element comprising: an element base plate consisting of apatite ceramics; first and second electrodes provided on said element base plate with said apatite ceramics being interposed therebetween; a third electrode provided on said element base plate with it being separated from said first and second electrodes; and a metal oxide provided between and in contact with said first and third electrodes, said metal oxide being at least one kind selected from the group consisting of tin oxide, zinc oxide, and composite oxide of titanium and niobium.

According to the present invention, in another aspect of it, there is provided a gas and humidity sensing element, in which use is made of a metal oxide doped with ruthenium oxide, or electrodes made of ruthenium oxide are printed and baked onto the base plate for the element.

The foregoing objects, other objects as well as the specific construction of the gas and humidity sensing element according to the present invention, the manner of fabricating the same, and its sensitivity characteristics will become more apparent and understandable from the following detailed description thereof when read in conjunction with the accompanying drawing.

BRIEF DESCRIPTION OF THE ACCOMPANYING DRAWING

In the drawing:

FIGS. 1 and 2 are respectively perspective views showing a construction of one embodiment of the gas and humidity sensing element according to the present invention, in which FIG. 1 indicates the front surface of the element, while FIG. 2 shows the rear surface thereof;

(Incidentally, the same reference numerals and symbols throughout the drawing designate identical or corresponding parts.)

DETAILED DESCRIPTION OF PREFERRED EMBODIMENTS

In the following, the present invention will be described with reference to several preferred examples thereof.

EXAMPLE 1

Figure 1:
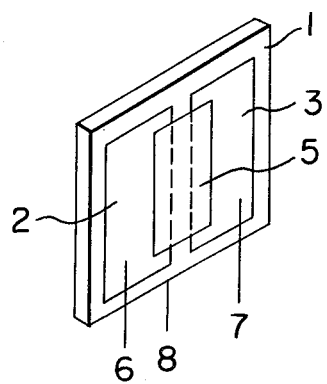

Hydroxy-apatite powder, with 10% of calcium (Ca) therein having been substituted for sodium (Na), was shaped under a pressure of 350 kg/cm$^2$ into an article having a dimension of 4 mm long, 4 mm wide, and 0.8 mm thick. This shaped body was then sintered in air for six hours at a temperature of 1,100° C. The sintered body was then polished to a thickness of 250 microns, followed by screen-printing of separate electrodes (first and third electrodes) (2), (3) made of RuO$_2$ in paste onto the front surface of the sintered body (1) as shown in FIG. 1, and an electrode (second electrode) (4) also made of RuO$_2$ in paste over the substantially entire portion of the rear surface of the same. Subsequently, paste of tin oxide (SnO$_2$) was screen-printed on a space 250 microns provided between the separate electrodes (2), (3). The paste of tin oxide (SnO$_2$) was prepared by sieving the powder of tin oxide, graded by a reagent to be highly pure, through a 400-mesh screen, and then adding butyl "Carbitol" (diethylene glycol monobutyl ether) to the sieved powder.

Following the screen-printing of the tin oxide paste, lead wires (6), (7) and (8) were attached to the respective electrodes (2), (3) and (4), and baked at 800° C. for ten minutes. The electrodes shaped in the abovementioned manner had porous surface so that moisture in the air may readily reach interior of the sintered body through the porous surface.

The base plate (1) for the element is made of humidity-sensing ceramics material such as hydroxy-apatite. The layer (5) of tin oxide constitutes the gas sensing material. When detecting bad smell gas and alcoholic gas, the element should be maintained at 200° C. and above. For this purpose, a coil heater made of "Kanthal" alloy wire is provided around the element shown in FIGS. 1 and 2, or two lead wires are attached to the electrode of RuO$_2$ covering the whole rear surface of the element in FIG. 2 so as to make it serve for both heater and humidity sensing electrode.

Figure 3:
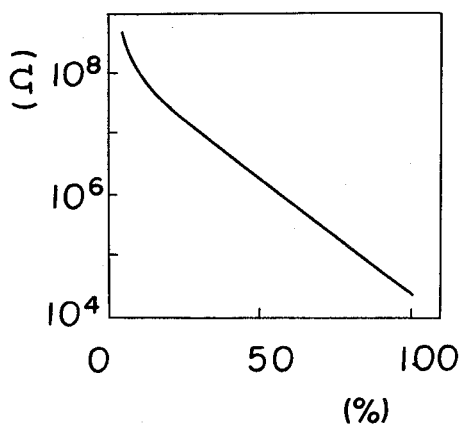
FIG. 3 is a graphical representation showing a humidity sensing characteristic curve of the gas and humidity sensing element according to the present invention.
Figure 4:
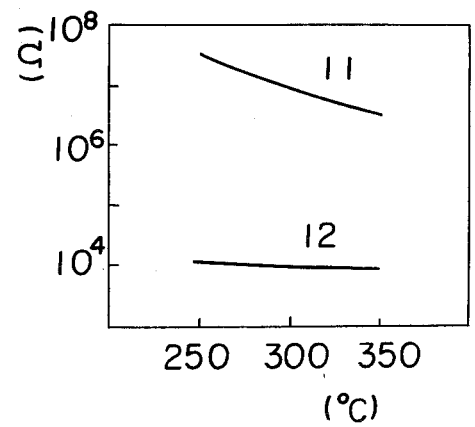
FIGS. 4 and 10 are respectively characteristic curves showing the temperature-dependent property of the gas sensing characteristic of the gas and humidity sensing element in each example of the present invention.
Figure 5:
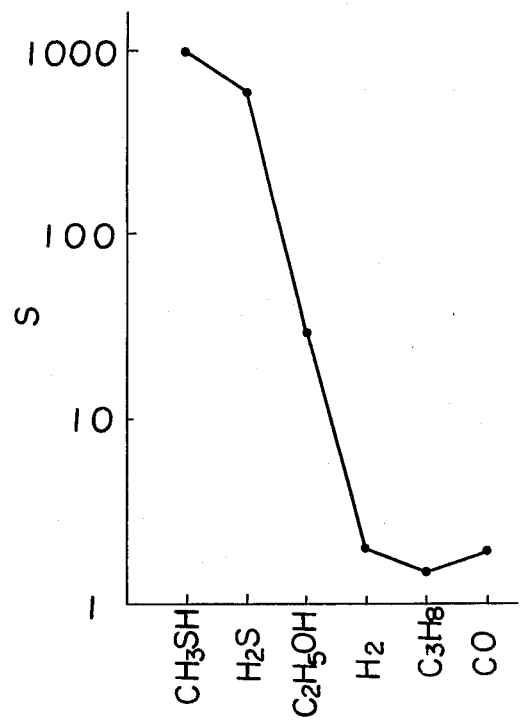
FIGS. 5, 7, 9, 11 and 13 are respectively characteristic polygonal lines showing sensitivity to various gases of the elements in each of the examples according to the present invention.

Then, by use of the gas and humidity sensing element manufactured in the abovementioned manner, measurements were carried out to obtain the results as shown in FIGS. 3 to 5.

FIG. 3 shows the humidity sensing characteristic of the element at 25° C. The measurement was carried out by short-circuiting the electrodes (2), (3) and then applying current in a sinusoidal waveform of 1 volt, 50 Hz across the electrodes (2), (3) and the electrode (4). Although it may be feasible to apply the voltage across one of the electrodes (2), (3) and the electrode (4) without short-circuiting the electrodes (2), (3), the electric resistance at the measurement would increase.

As seen from the characteristic curve in FIG. 3, the electric resistance varies over the four numerical places and more at the relative humidity in a range of from 0 to 100%, which indicates that the sensitivity of the element is high. Further, variations in the sensing characteristics were within the permissible error of measurement even after the element had been left in a laboratory for consecutive six months with electric conduction of 1 volt, or without any conduction at all, which proved that the element was highly stable. This is the characteristic which cannot be seen in other sorts of ceramic humidity sensor. The response speed of the element was also as quick as 2 to 15 seconds.

FIG. 4 shows the gas sensing characteristic of the element when the temperature of the element was varied. The electric resistance across the electrodes (2) and (3) was measured. The characteristic curve (11) is for the measured results of the electric resistance with the methyl mercaptan (CH$_3$SH) concentration in the air of zero ppm, while the curve (12) is for the electric resistance with the concentration of 100 ppm of the same.

As seen from FIG. 4, the electric resistance values changed in two to three numerical places and more between the two characteristic curves (11) and (12).

FIG. 5 shows the sensitivity S of the element to 100 ppm concentration of each of methyl mercaptan (CH$_3$SH), hydrogen sulfide (H$_2$S), ethyl alcohol (C$_2$H$_5$OH), hydrogen (H$_2$), carbon monoxide (CO), and propane (C$_3$H$_8$). When the resistance value in the atmosphere is Ra and that in 100 ppm concentration of each gas is Rg, the sensitivity S is represented by Ra/Rg, which denotes a quantity of change in the resistance value. In FIG. 5, the element was maintained at a temperature of 300° C. As seen from the graphical representation in FIG. 5, the element hardly showed its sensitivity to hydrogen (H$_2$), carbon monoxide (CO) and propane (C$_3$H$_8$), while it showed substantially same degree of sensitivity to methyl alcohol, ispropyl alcohol, etc. as it did to ethyl alcohol.

Since apatite has high gas adsorptibility, there is a high possibility of its contribution to high sensitivity and selectivity to the gases.

EXAMPLE 2

The first half of the fabrication steps was the same as that in Example 1 above. The second half of the fabrication steps was, however, different in the shaping step of the gas sensing material. The gas sensing material was tin oxide (SnO$_2$) in paste containing therein 0 to 50% by weight of ruthenium oxide (RuO$_2$), which was screen-printed on the same position of the base plate for the element as in Example 1 above. The paste was prepared by crushing tin oxide (SnO$_2$) graded by a reagent to be specially pure, sieving the pulverized material through a 400-mesh screen, followed by admixing ruthenium oxide (RuO$_2$) therewith, and adding butyl "Carbitol" to the powder mixture. After the screen-printing, lead wires (6), (7) and (8) were attached to each of the printed electrodes and baked for ten minutes at 800° C. As is the case with Example 1 above, the gas and humidity sensing element is constructed with the base plate (1) made of humidity sensitive ceramics of hydroxy-apatite, the electrodes (2), (3) and (4) made of ruthenium oxide (RuO$_2$), the gas sensitive material (5) composed of (SnO$_2$+RuO$_2$), and the lead wires (6), (7) and (8).

Figure 6:
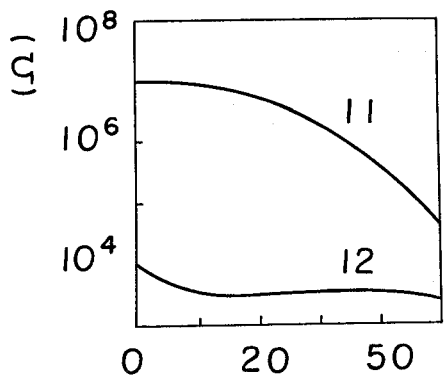
FIGS. 6, 8 and 12 are respectively characteristic curves showing the $RuO_2$ content dependent property of the gas sensing characteristic of the sensing element in each example of the present invention.
Figure 7:
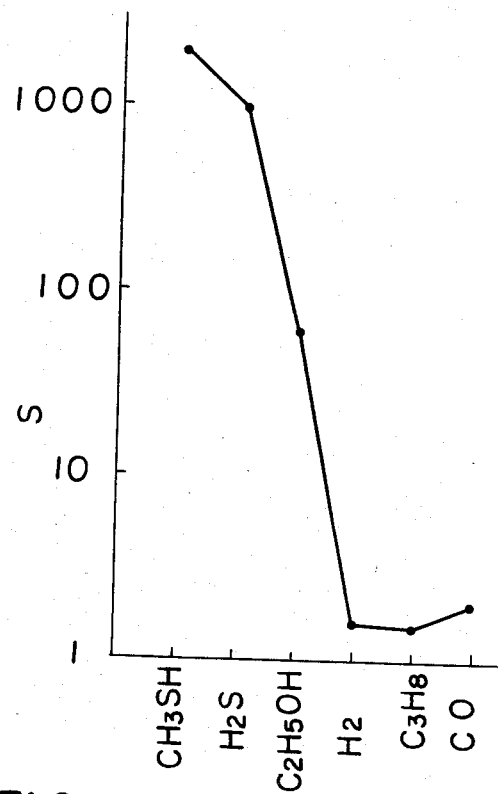

With this gas and humidity sensing element using the gas sensing material composed of (SnO$_2$+RuO$_2$), the measurements were conducted to obtain the results as shown in FIGS. 6 and 7. FIG. 6 shows a relationship between the gas sensitivity characteristic of the element to methyl mercaptan (CH$_3$SH) and the content of RuO$_2$, when the sensing element was maintained at 300° C. It should be noted here that, even if the content of RuO$_2$ is nil in the element base plate, there are provided on the element the electrodes (2), (3) made of a material containing RuO$_2$ as the principal constituent. The electrical resistance across the electrodes (2) and (3) in FIG. 1 was measured. The characteristic curve (11) in FIG. 6 is for the measured results of the electrical resistance with the methyl mercaptan ($CH_3SH$) concentration of zero ppm in the atmosphere, while the characteristic curve (12) is for the electrical resistance with the methyl mercaptan concentration of 100 ppm in the atmosphere. The element containing therein 10% by weight of $RuO_2$ showed a sensitivity of approximately 2,000 times as high as that of ordinary sensing elements. When the $RuO_2$ content ranges from 40 to 50% by weight, the electric resistance value in the atmosphere lowers, hence the sensitivity of the element. The "sensitivity" as referred to herein is a ratio between the electric resistance value Ra in the atmosphere and the electric resistance value Rg in the methyl mercaptan ($CH_3SH$) concentration of 100 ppm. In FIG. 6, the $RuO_2$ content of zero percent by weight exactly stands for the element in Example 1 above.

FIG. 7 indicates the sensitivity S of the sensing element with the concentration of 100 ppm of each of methyl mercaptan ($CH_3SH$), hydrogen sulfide ($H_2S$), ethyl alcohol ($C_2H_5OH$), hydrogen ($H_2$), propane ($C_3H_8$), and carbon monoxide (CO), at the element temperature of 300° C. and the $RuO_2$ content of 10% by weight. As seen from the graphical representation in FIG. 7, the element showed almost no sensitivity to the gases to any appreciable degree, except for methyl mercaptan ($CH_3SH$), hydrogen sulfide ($H_2S$) and ethyl alcohol ($C_2H_5OH$). The element showed substantially equal degree of sensitivity to alcohols such as methyl alcohol, isopropyl alcohol, etc. as it did to ethyl alcohol.

Incidentally, the results of measurement in FIG. 3 for Example 1 above equally applies to the results of measurement even in this Example 2, hence any detailed explanations thereof will be dispensed with.

EXAMPLE 3

The first half of the fabrication steps was done under the same conditions as in Example 1 above. The second half of the fabrication steps was, however, different in its step of shaping the gas sensing material. That is, the gas sensing material is zinc oxide (ZnO) in paste containing therein 0 to 50% by weight of ruthenium oxide ($RuO_2$), which was screen-printed on the same position of the element base plate as in Example 1 above. This paste was prepared by crushing zin oxide (ZnO) graded by a reagent to be specially pure, sieving the pulverized zinc oxide through a 400-mesh screen, followed by doping ruthenium oxide ($RuO_2$) with it, and adding butyl "Carbitol" to the powder mixture. After the screen-printing of the paste, lead wires (6), (7) and (8) were attached to the thus printed electrodes and baked for ten minutes at 800° C. The gas and humidity sensing element thus fabricated is constructed with the base plate (1) of humidity sensitive ceramics of hydroxy-apatite, the electrodes (2), (3) and (4) made of ruthenium oxide ($RuO_2$), the gas sensitive material (5) consisting of ($ZnO+RuO_2$), and the lead wires (6), (7) and (8).

Figure 8:
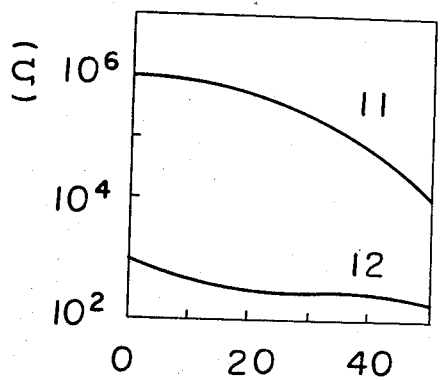
Figure 9:
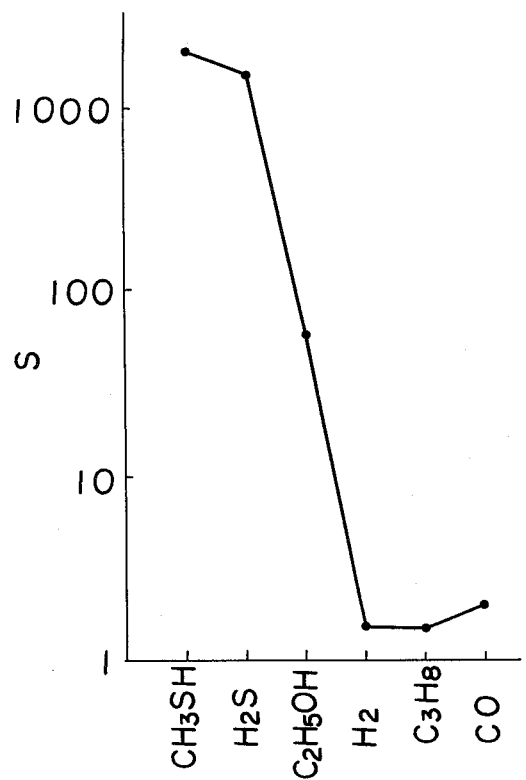

The results of measurements with the gas and humidity sensing element using the gas sensitive material of ($ZnO+RuO_2$) are as shown in FIGS. 8 and 9 which correspond respectively to FIGS. 6 and 7 for the results of measurements in Example 2.

According to the element of this Example 3, the sensitivity thereof to methyl mercaptan is approximately 2,000 times as high as that of ordinary sensing elements, since it contains therein 10% by weight of $RuO_2$ same as the element in Example 2, and its response speed at the methyl mercaptan concentration of a range of from 0 to 100 ppm is as quick as one second. Incidentally, the temperature of the element at the measurements in FIGS. 8 and 9 was 450° C. Ethyl alcohol is representative of the alcohols for the purpose of the measurement in this particular example, through the element showed substantially same degree of sensitivity to other alcohols such as methyl alcohol, isopropyl alcohol, and so forth as it did to ethyl alcohol.

By the way, the results of measurements in this Example 3 are the same as the results of measurement in Example 1 above shown in FIG. 3, hence any detailed description thereof will be dispensed with.

EXAMPLE 4

The first half of the fabrication steps was done under the same conditions as in Example 1 above. The second half of the fabrication steps, however, was different in respect of the step of shaping the gas sensitive material. For the gas sensitive material, there was used a composite oxide of titanium and niobium in paste form, which paste was screen-printed on the surface of the element base plate.

Figure 2:
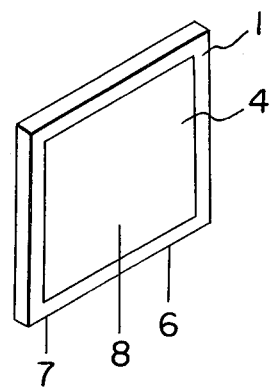

The paste was prepared by mixing titanium oxide ($TiO_2$) and niobium oxide ($Nb_2O_5$) at a mol ratio of $0.5 \leq Nb/Ti \leq 4$, or preferably $Nb/Ti=2$, sintering the mixture in the atmosphere for two hours at a temperature of 1,300° C., crushing the sintered material followed by its passage through a 400-mesh sieve, and adding butyl "Carbitol" to the sieved powder material. After the screen-printing of the abovementioned composite oxide paste onto the element base plate, lead wires (6), (7) and (8) were attached as shown in FIGS. 1 and 2, and baked for ten minutes at 800° C.

The electrodes formed in the above-described manner had porous surface so that moisture in the atmosphere may readily reach inside the sintered body through the porous surface. The gas and humidity sensing element thus fabricated is constructed with the element base plate (1) made of a humidity-sensitive ceramics of hydroxy-apatite, the gas sensitive material consisting of the composite oxide of titanium and niobium, and the lead wires (6), (7) and (8).

Figure 10:
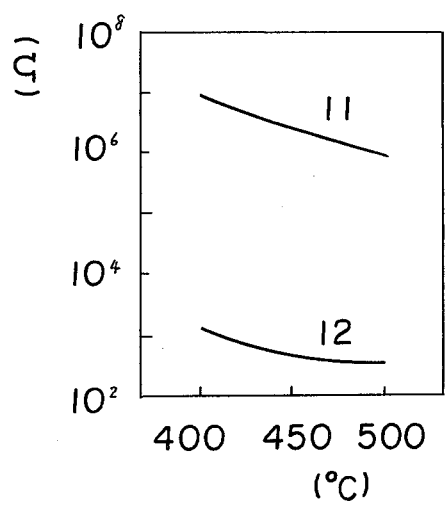

FIG. 10 is a graphical representation showing the gas sensitive characteristic of the element when its temperature was varied, in which the electrical resistance across the electrodes (2) and (3) was measured. The characteristic curve (11) in FIG. 10 indicates the electric resistance with the methyl mercaptan concentration of zero ppm in the atmosphere, while the curve (12) is for the electric resistance with the methyl mercaptan concentration of 100 ppm. As seen from the graphical representation, the resistance values changed in three numerical places and more between the two characteristic curves (11) and (12).

Figure 11:
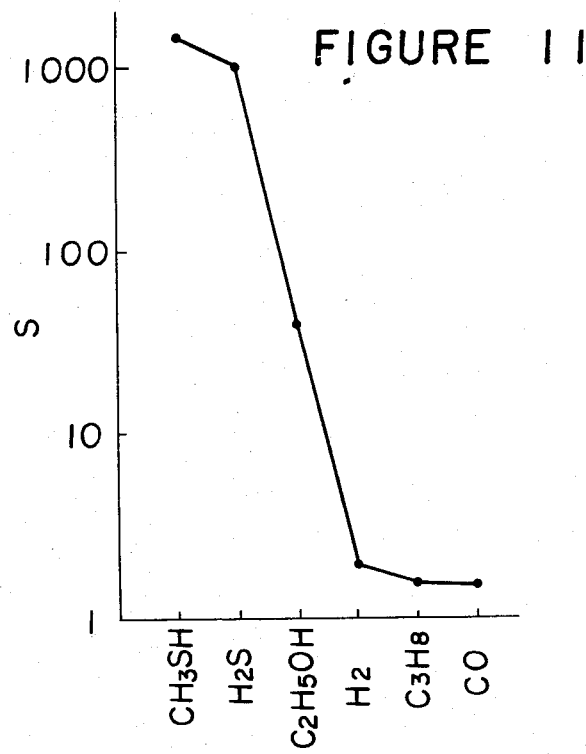

FIG. 11 shows the sensitivity S of the gas and humidity sensing element to each of methyl mercaptan ($CH_3SH$), hydrogen sulfide ($H_2S$), ethyl alcohol ($C_2H_5OH$), hydrogen ($H_2$), carbon monoxide (CO), and propane ($C_3H_8$) at the concentration of 100 ppm in the atmosphere. When the electrical resistance value of the element in the atmosphere is Ra and that in the gas at its concentration of 100 ppm is Rg, the sensitivity S is represented by Ra/Rg, which denotes a quantity of change in the resistance value. The sensitivity in FIG. 11 is one at the element temperature of 450° C. The element showed no substantial sensitivity to hydrogen ($H_2$), carbon monoxide (CO), propane ($C_3H_8$) and other inflammable gases. However, it showed substantially same degree of sensitivity to methyl alcohol, isopropyl alcohol, etc. as it did to ethyl alcohol.

The results of measurements in this Example 4 was the same as those in Example 1 shown in FIG. 3, hence any detailed description thereof will be dispensed with.

EXAMPLE 5

The first half of the fabrication steps was done in the same manner as in Example 1 above. The second half of the fabrication steps was, however, different in the step of shaping the gas sensing material. That is to way, the gas sensing material forming paste is a mixture of ruthenium oxide ($RuO_2$) and a composite oxide of titanium and niobium, in which mixture the $RuO_2$ content is in a range of from 0 to 50% by weight.

After this paste was screen-printed on the same position of the base plate for the sensing element as in Example 1 above, lead wires (6), (7) and (8) were attached to the screen-printed electrodes as shown in FIG. 2, and baked for ten minutes at 800° C. In this way, the gas sensing material (5) can be composed of the composite oxide and ruthenium oxide.

Figure 12:
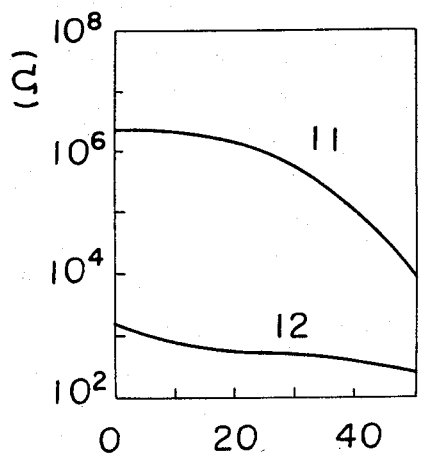
Figure 13:
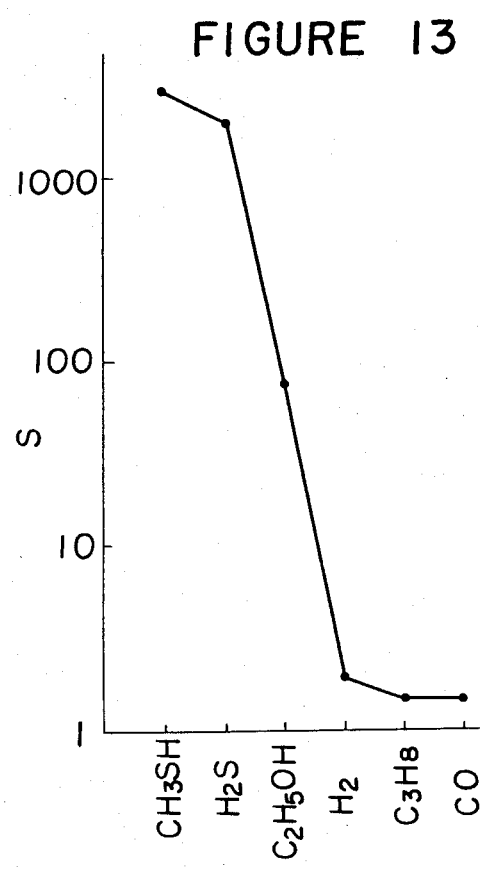

Using the gas and humidity sensing element fabricated in the above mentioned manner, measurements were conducted to obtain the results as shown in FIGS. 12 and 13. FIG. 12 is a graphical representation showing a relationship between the gas sensitivity characteristic to methyl mercaptan and the content of ruthenium oxide, when the sensing element was maintained at 450° C. It should be noted here that, even when the base plate of the element contains no ruthenium oxide, there are provided on the element the electrodes (2), (3) made of ruthenium oxide as the principal constituent. In the graphical representation in FIG. 12, the characteristic curve (11) indicates the measured results of electrical resistance with the methyl mercaptan concentration in the atmosphere of zero ppm, while the characteristic curve (12) therein indicates the measured results of electrical resistance with the methyl mercaptan concentration of 100 ppm. The element containing therein 10% by weight of ruthenium oxide showed its sensitivity of 3,000 times as high as that of ordinary sensing elements. When the content of ruthenium oxide reaches 40 to 50% by weight, the electrical resistance of the element in the atmosphere lowers, hence the sensitivity thereof.

FIG. 13 indicates the measured results corresponding to those of Example 2 shown in FIG. 7. In this case, the element was maintained at a temperature of 450° C., and contained therein 10% by weight of ruthenium oxide. As seen from the graphical representation in FIG. 13, the element did not show its sensitivity to the inflammable gases, except for alcohol, such as hydrogen ($H_2$), carbon monoxide (CO), propane ($C_3H_8$), and others to any appreciable extent. However, it showed as equal a sensitivity to methyl alcohol, isopropyl alcohol, etc. as it did to ethyl alcohol. Its response to methyl mercaptan ($CH_3SH$) at the concentration of from 0 to 100 ppm was as quick as 1 second.

Since apatite has high adsorptibility with gas, there is high possibility that the substance contributed to the high sensitivity and high selectivity to the gases.

By the way, since the measured results corresponding to FIG. 3 for Example 1 above exactly applies to the results of measurement to the case of Example 2, any detailed explanations of the measured results will be dispensed with.

The foregoing preferred examples of the present invention are all for the case of using hydroxy-apatite as the apatite material. It should, however, be understood that any other apatite material such as, for example, those in which the hydroxy group is substituted for halogen, or those in which calcium is substituted for strontium, barium, lead, and so forth may be equally used. Furthermore, FIGS. 1 and 2 illustrate the gas and humidity sensing element in the planar shape, but it may be shaped in a cylindrical form with the inner surface thereof being entirely cotaed with the electrode, and the other surface thereof being provided with the separate electrodes, the gas sensing material in paste being interposed between these separate electrodes.

In the foregoing, the present invention has been described with specific details in reference to several preferred examples thereof. It should, however, be noted that these examples are illustrative only and not so limitative, and that any changes and modifications may be made by those skilled in the art within the spirit and scope of the invention as recited in the appended claims.

We claim:

1. A gas and humidity sensing element comprising: an element base plate consisting of apatite ceramics; first and second electrodes provided on said element base plate with said apatite ceramics being interposed therebetween; a third electrode provided on said element base plate with it being separated from said first and second electrodes; and a metal oxide provided between and in contact with said first and third electrodes, said metal oxide being at least one kind selected from the group consisting of tin oxide, zinc oxide, and composite oxide of titanium and niobium.

2. The gas and humidity sensing element according to claim 1, wherein said metal oxide is doped with ruthenium oxide.

3. The gas and humidity sensing element according to claim 2, wherein said first and third electrodes consist of ruthenium oxide, which is printed and baked on said element base plate.

4. The gas and humidity sensing element according to claim 1, wherein said electrodes have porous surface.

5. The gas and humidity sensing element according to claim 1, wherein said first and third electrodes consist of ruthenium oxide, which is printed and baked onn said element base plate.